(12) United States Patent
Roreger et al.

(10) Patent No.: US 6,818,087 B1
(45) Date of Patent: Nov. 16, 2004

(54) METHOD FOR PRODUCING LAMINATED SHEET MATRIX CONTAINING RELEASABLE INGREDIENT

(75) Inventors: Michael Roreger, Neuwied (DE); Malgorzata Kloczko, Linz (DE)

(73) Assignee: ECS Environment Care Systems GmbH, Andernach (DE)

( * ) Notice: Subject to any disclaimer, the term of this patent is extended or adjusted under 35 U.S.C. 154(b) by 0 days.

(21) Appl. No.: 09/914,866

(22) PCT Filed: Feb. 22, 2000

(86) PCT No.: PCT/EP00/01438
§ 371 (c)(1),
(2), (4) Date: Oct. 9, 2001

(87) PCT Pub. No.: WO00/51815
PCT Pub. Date: Sep. 8, 2000

(30) Foreign Application Priority Data

Mar. 4, 1999 (DE) .......................... 199 09 493

(51) Int. Cl.[7] .................... B32B 31/00; B05D 5/00; A01M 1/00; A01N 25/34; A61K 31/66
(52) U.S. Cl. .................... 156/145; 156/146; 156/276; 156/295; 427/286; 427/375; 427/428; 428/304.4; 428/907; 43/132.1; 424/84; 514/122
(58) Field of Search ................. 156/745, 146, 156/147, 228, 276, 295, 230, 240; 427/2.1, 208, 286, 372.7, 375, 421, 428; 428/304.4, 907; 43/111, 132.1; 424/84; 514/122, 748

(56) References Cited

U.S. PATENT DOCUMENTS

| 3,625,875 A | * | 12/1971 | Fraugenglass et al. .... 260/17 A |
| 4,666,767 A | * | 5/1987 | Von Kohorn et al. .... 428/304.4 |
| 4,990,381 A | | 2/1991 | Holzner |
| 5,368,943 A | * | 11/1994 | Baghdachi et al. ...... 428/423.1 |
| 5,792,513 A | * | 8/1998 | Koslow et al. |

FOREIGN PATENT DOCUMENTS

| DE | ST 2423 IVB/55 F | | 9/1952 | |
| DE | 195 32 489 | | 3/1997 | |
| GB | 2098541 | * | 11/1982 | |
| GB | 2131740 | * | 6/1984 | |
| GB | 2131740 A | * | 6/1984 | ........... B32B/33/00 |

* cited by examiner

Primary Examiner—J. A. Lorengo
(74) Attorney, Agent, or Firm—Jordan and Hamburg LLP

(57) ABSTRACT

A sheetlike article comprising a single-layer homogenous matrix containing at least one active substance such as a crop protection agent, biocide, fertilizer, plant strengthener, cosmetic substance or fragrance, is produced by applying the at least one active substance to at least one of two layers of identical composition, placing the two layers atop one another so as to enclose the at least one active substance, irreversibly joining the layers with the at least one active substance therebetween under pressure to form a laminate and storing the laminate under defined conditions for a duration sufficient to effect migration of the at least one active substance into the base layer and connection of the layers at their interfaces.

39 Claims, 2 Drawing Sheets

METHOD FOR PRODUCING LAMINATED SHEET MATRIX CONTAINING RELEASABLE INGREDIENT

BACKGROUND OF THE INVENTION

The invention relates to a process for producing a sheetlike formulation comprising at least one single-layer active substance matrix for the controlled release of active substance to the vicinity of the application site, the active substances being selected from crop protection agents, biocides, fertilizers, plant strengtheners, cosmetic active principles and fragrances.

Formulations, whose preparation is described below, are known from many areas of life for which the time- and quantity-controlled release of one or more active substances is required. Depending on the area of use, these formulations are applied in the form of sheetlike structures such as labels, strips, pouches, plasters or plaques to certain substrates or objects from which they develop their action. Typical fields of use for such products that may be mentioned here include, for example, pest control, for example, in vineyards or in forestry, or for crop protection, perfumery and cosmetology.

For reasons of cost, such formulations are wherever possible formulated so that the active substance is contained in a flat, single-layer polymer film from which in the course of the use the active substance is released to the site or the vicinity of application. In general, these formulations have a layered structure, comprising at least one matrix layer containing active substance and at least one support layer in contact with the matrix layer. These layers can be present in a "sandwich-like" form or are joined to one another at the sides and formed in the manner of a pouch. Depending on the field of use, they are usually also in fixed or detachable combination with different functional layers such as, for example, control membranes or protective layers.

Processes for producing formulations of the type specified are known. A common feature of such preparation processes known from practice is that the formulation is first of all produced in the form of a strip-shaped web embracing the active substance matrix, then combined, if desired, with other layers, and separated into sections of a desired size by punching or cutting.

Because of the diversity of active substances applicable by means of these devices, and because of the different physicochemical properties of these active substances, the preparation of the single-layer active substance matrix represents the central step in such processes. Among the prior art processes for the preparation of such formulations, the dissolving or dispersing of the active substances in matrix material, usually a polymer solution or polymer melt, with subsequent drying, is probably the process of choice for the person skilled in the art. However, not all active substances can be processed in this way. The processing of volatile active substances proves to be particularly problematic, since the evaporation of the active substance during the preparation is almost impossible to control. And temperature-sensitive, so-called thermally labile active substances can be used only with restrictions, if at all, for systems requiring heat treatment during the manufacturing process.

For this reason, a variety of solutions have been worked out over the course of time to allow the preparation of the releasing matrices, especially for volatile and/or thermally labile active substances. For example, the principle of a depot is used, in which problematic active substances are introduced into a multi-part product in the form of a discrete reservoir of active substance without thermal stress—for example, in a separate process step during preparation. Processes of this kind in which the preparation of matrix layers free from active substance and the introduction of the active substance into the product take place as temporally and spatially separate operating steps are known from the manufacture of numerous products but are very labour-intensive.

In accordance with the prior art, active substance can be incorporated into a matrix using a variety of techniques. For instance, the introduction of a flowable active substance medium under pressure, in addition to the pressurized insertion of a solid active substance body, and injection, belongs to known processes of incorporating active substance into solid matrices. The processes mentioned have the common feature that active substance is applied initially to a support on which it remains only temporarily, since it migrates into the matrix layers that are in contact with it. Constituents which prevent unwanted flow or escape and whose function is to halt the active substance temporarily are referred to in the technical literature using terms such as, for example, adsorption layer, active substance dispenser, active substance support, fixing aid, support material, and interlayer. Liquid-absorbing substrates suitable for this purpose include nonwoven, foam, paper or woven textile material.

In practice, however, known production processes are frequently associated with disadvantages, a selection of which is specified below, and, as a result, prove to be correspondingly complex:

The absorption capacity for liquid media is generally limited to a certain level, which is frequently a limiting factor in loading the matrix with active substance.

In order to obtain controlled, continuous release of active substance over prolonged periods of application and to rule out the possibility of unwanted side-effects caused by excessive release rates, an additional control layer is often necessary.

The use of additional materials prolongs production and complicates it technically, since the individual layers and elements must first be manufactured separately from one another and then combined with one another in one or more subsequent steps.

The use of additional elements may also impair the performance qualities of the product, especially the shear stability, since the incorporation of an active substance fixing means reduces the contact area between matrix layers which are to be united. In order to ensure, despite this, the desired structural integrity of the formulation, there is often a need for additional connecting areas, in the form, for example, of a peripheral adhesive edge, which result in an unwanted increase in the dimensions.

The embedding of additional support materials may, furthermore, adversely affect the flexibility and functionality of the product. This is particularly so if thicker layers are necessary as a result of a low absorptive capacity, e.g. the absorbency of the material. These disadvantages are extremely undesirable especially in the case of active substance patches applied to surfaces of plants.

The morphology of the higher plants, especially the low radius of curvature and the lack of evenness and cleanliness of surfaces of plants, indeed, imposes particularly stringent requirements on the flexibility and small dimensioning of such active substance formulations. Added to this are the severe conditions borne by the surfaces of plants as a result of natural weather conditions at the site of application, which increases their susceptibility to a possible loss of cohesion.

SUMMARY OF THE INVENTION

Because of the disadvantages described above, multilayer or multipart formulations cannot be used for a number of applications on account, firstly, of their functionality. Secondly, the production costs resulting from the relatively high level of expenditure of material and manufacture limit the marketability and acceptance of such products. For price-sensitive markets and those where competition is intense, in particular, it would be desirable to be able to offer inexpensive products of comparatively simple construction for temperature-sensitive and volatile active substances as well.

The object of the invention is therefore to provide a process for producing sheetlike active substance formulations comprising a single-layer matrix, containing active substance, for the controllable release of active substances, including volatile and temperature-sensitive substances, which avoids the disadvantages of the processes known from the prior art.

This object is achieved in accordance with the invention by means of a production process utilizing process steps described in detail below.

A process is proposed in which the single-layer active substance matrix of the device is produced using at least two layers, identical in composition, of a base material in the following component steps which are separated from one another temporally and spatially (ref rence numerals in accordance with FIG. 1):
a) provision of two prefabricable layers (1, 2), identical in composition, of a base material,
b) application of active substance to at least one of the two layers (1, 2),
c) placement of the two layers (1, 2) atop one another so as to enclose the active substance applied, and irreversible joining under pressure to form a laminate,
d) storage of the laminate for predeterminable duration under defined conditions, with migration of the active substance into the base layers (1, 2), and connection at their interfaces to form a homogenous matrix featuring substantially uniform dispensation of active substance.

Active substances incorporated by this process into the matrix of the formulation include, for example, crop protection agents, biocides, fertilizers, plant strengtheners, cosmetic active principles and fragrances. The matrix layers can comprise one or more active substances.

"Biocides", according to the EC Biocides Directive, which has been in force since 14 May 1998, are substances or formulations which as intended possess the capacity to kill living organisms or at least to restrict them in their vital function. They are used, inter alia, as wood preservatives, disinfectants, process preservatives, insecticides and rodenticides. The term "crop protection agents", which in the present specification is used synonymously with "pesticides", and also the term "plant strengtheners", are defined in §2 of the Crop Protection Act applying in Germany.

The term "volatile substances" refers to substances having an effective vapour pressure even at room temperature. Examples that may be mentioned include insecticidal compounds such as dimethoate and acephate or insect pheromones such as Z,E-9,1.2-tetradecadienol and Z,E-9,12-tetradecadien-1-yl acetate.

For the purposes of the present invention, the term "temperature-sensitive" or "thermally labile" substances refers to substances which decompose, or whose biological activity is impaired, at a temperature $\geq 50°$ C.

In the process of the invention, the single-layer active substance matrix comes about through direct introduction of active substance between identical matrix layers, which are subsequently united by pressure and stored for the purpose of "maturation". The principal advantage of this process lies in its avoidance of the use of additional active substance fixing aids, thereby considerably reducing the expenditure on material and manufacture and at the same time significantly improving the functional quality of the products produced in this way. As a manufacturing process which proceeds at room temperature, this process is of particular value for the production of devices comprising volatile and thermally labile substances.

Advantageous embodiments of the process according to the main claim can be inferred by the person skilled in the art from the features of the subclaims. They relate, for example, to volumetric metering of the active substance, the operating pressure required when active substance is admitted into the matrix layer, further process parameters associated with the "maturation" of the matrix, the way in which the active substance is introduced and applied, the material basis of the matrix base material, particular properties of the active substance, and its designations.

BRIEF DESCRIPTION OF THE INVENTION

DETAILED DESCRIPTION OF THE INVENTION

Figure 1:
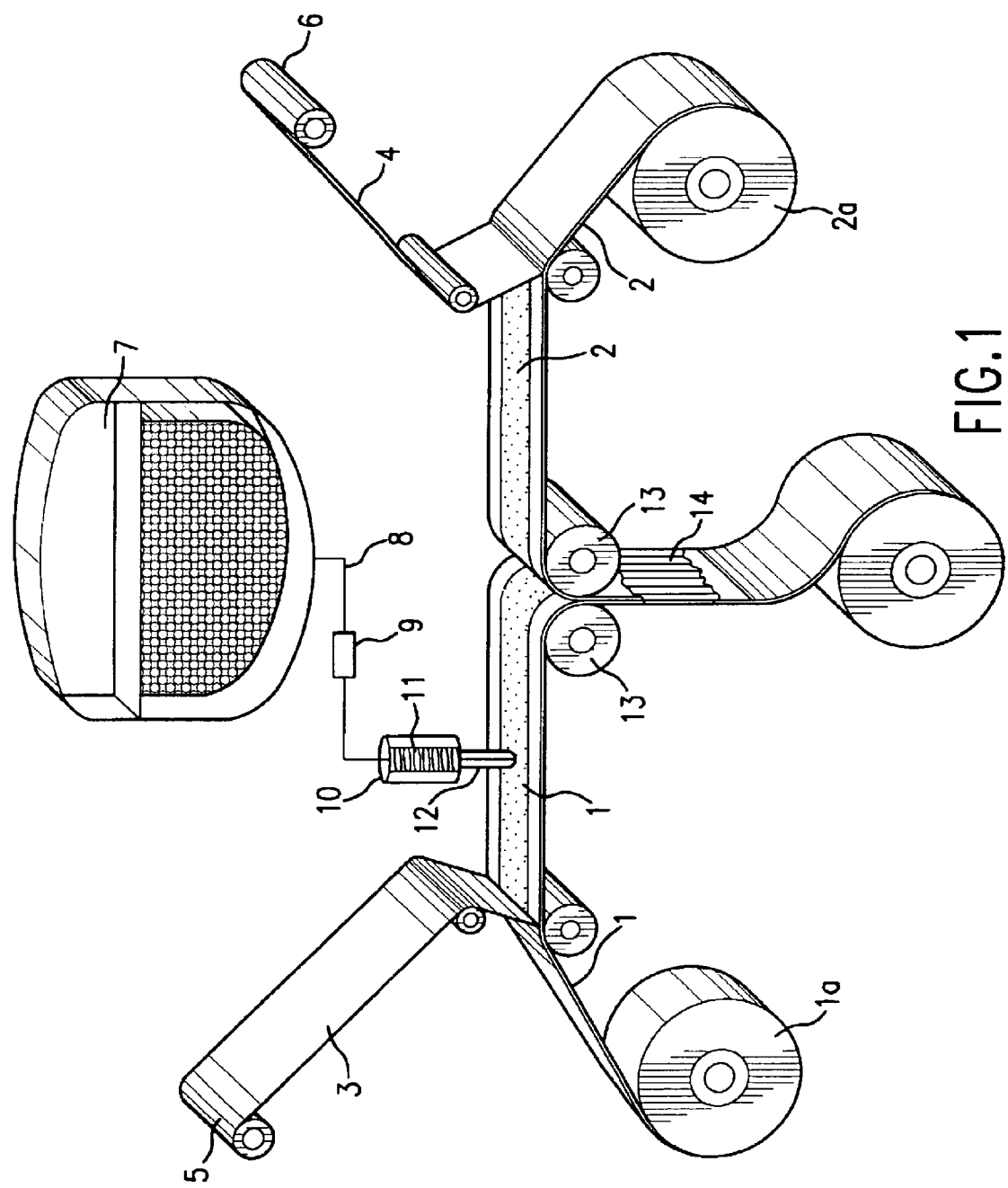
FIG. 1 is a schematic process flowchart.

In FIG. 1, (1) and (2) denote identical layers of the matrix base material, which are present as strip-shaped webs in the form of laminates on stock rolls (1$a$; 2$a$). Judiciously, both layers (1, 2) are provided on both sides with protective layers (3, 4), of which at least one (3) is detachable. The protective layers (3, 4) can consist of various materials such as paper, plastic and textiles, but to must—by means, for example, of treatment with silicone be rendered detachable. This is particularly important if the matrix layers (1, 2) are self-adhesive. Prior to the application of the active substance, both prefabricated base material layers (1, 2) are exposed by the removable protective layers (3, 4) being peeled off and taken up by corresponding winders (5, 6).

Another configuration possibility for the process of the invention consists, for example, in the base material layers (1, 2) being provided only with one web, which is treated so as to repel the matrix on both sides, and being therefore present in the form of laminate rolls "wound in on themselves".

In the process of the invention, active substance is metered in the form of a flowable medium. The active substance medium is in a stock container (7) which is connected via a hose (8) to a metering station (10). The active substance medium is therefore located within a closed system, which is of decisive importance in the case of volatile substances in particular.

Conveyance of the active substance medium into the metering station (10) is the function of a feed unit (9), which in the case of the process of the invention can be a hose pump, for example. However, it is also possible to use other kinds of pump suitable for metering, such as gear, screw, centrifugal or reciprocating pumps. It is essential for the purposes of the invention that the feed unit ensures pulseless conveying with a meterable conveyed quantity and constant pressure. A uniform conveyed flow is vital for uniform supplying of the metering station (10) with the active substance medium.

In the process of the invention, the metering station (10) consists, for example, of an active substance dispenser (11) and one or more applicator nozzles (12). The active substance dispenser (11) used in the process of the invention can comprise, for example, so-called NEMO Robo dispensers operating in accordance with the principle of rotating positive-displacement pumps. This functional principle of the dispenser is advantageous for the production process in that the conveyed amount of active substance medium is directly dependent on the rotor speed; it can be altered steplessly and adapted without problems to the requirements of the process. Different-sized constructions can be assigned different "metered-amount ranges"; as a result of the rotary mode of operation, the pressure exerted on the active substance medium remains constant.

Observing the uniform pressure, which is $\leq 12$ bar, is of essential importance to the invention in terms of metering accuracy.

A further advantage of this dispenser (11) lies in the possibility of reversing the conveying direction, which results in a short break in the thread. This prevents the accumulation of medium at the endpoints of the application and ensures uniform distribution of the active substance medium on the weblike matrix (14).

This is of particular importance for formulations in accordance with the process of the invention. Nonuniform distribution of the active substance between the base material layers (1, 2) would result in a nonhomogenous distribution of active substance in the matrix of the finished product and would, ultimately, have an adverse effect on the desired active substance release profile.

In this process, uniform distribution of the active substance formulation is the function of the applicator nozzles (12). Their number and arrangement are chosen so that the available matrix area is provided evenly with active substance medium. Judiciously, the application can be arranged in patterns such as stripes, dots, circles or other geometric shapes. These patterns can be produced in either intermittent or rotary operating mode, preference being given to the latter mode since it generally permits higher production rates.

In the production process of the invention, active substances are metered in the form of a flowable medium whose viscosity can vary within wide limits but is at least 1000 mPa.s. Indeed, in the case of liquids of low viscosity, there can be unwanted flow of the medium on the matrix. This adverse effect would be intensified further in the course of the subsequent lamination under pressure. For establishing the desired minimum viscosity, viscosity-increasing additives such as, for example, AEROSIL® or polymers are useful, which can be either of natural origin, such as gelatine or derivatives of starch, for example, or of synthetic origin, such as polyacrylic acid, for example.

In order to establish the desired viscosity range it is judicious to thermally condition the application equipment.

In accordance with the invention, the laminating operation, which takes place directly after the metering of the active substance, can be performed at a pressure of between 2 and 10 bar. A particularly advantageous pressure range is that from 3 to 5 bar. In lamination, both base material layers (1, 2) are joined and irreversibly bonded under the effect of pressure. It is necessary to choose the laminating pressure such that the active substance medium does not emerge at the edges of the weblike matrix (14) and such that the interfaces of the base material layers (1, 2) are bonded inseparably.

A particularly advantageous possibility for configuring the production process of the invention consists in that base material layers (1, 2) and the matrix (14) formed from them have been made self-adhesive. This significantly facilitates the formation of the single-layer matrix (14) and additionally increases the shear stability of the finished product.

When the production process is carried out, the active substance medium can also have adhesive properties. A person skilled in the art can readily achieve this by means of tackifying additives, such as resins, for example.

The matrix-forming layers (1, 2) which are used in the process can consist of different materials. It is essential to the invention, however, that they are identical in terms of their composition and include a polymer or polymer mixture.

Suitable polymers in principle are all those which are able to take up and releas active substances and which can be processed to films. The following groups may be mentioned as particularly suitable matrix polymers: ethylene-vinyl acetate copolymers, block copolymers, e.g. styrene/butadiene/styrene or styrene/isoprene/styrene, polyisobutylene, polyacrylates, polymethacrylates, polyvinyl esters, polyamide, polyesters, cellulose derivatives and silicones.

The selection of the polymer for base material layers (1, 2) is guided by the chemical and physical properties of the active substance.

Depending on the use of the formulation according to the invention, active substances from different groups can be used, such as crop protection agents, biocides, fertilizers, plant strengtheners, cosmetic active principles and fragrances, for example. The active substances, which following metering and lamination are firmly enclosed in the middle of the matrix (14), diffuse, in accordance with FIG. 2 and in agreement with Fick's laws of diffusion, until they have attained a substantially uniform distribution within the matrix (14). This process, which is referred to as "maturation", is specific to the active substance and dependent on both time and temperature, and can be determined by the person skilled in the art. Advantageous embodiments comprise one or more of the active substances dimethoate, imidacloprid, fenpropidine, acephate and acetamiprid.

The duration of this phase of the production process of the invention can be shortened to a desired time by way of the nature of the operating parameters during storage of the laminate. It is important, however, that the storage temperature does not exceed the critical range for the active substance in question. The range 15–30° C. and, in particular, 20–24° C. may be mentioned as a favourable storage temperature.

In a modification of the process of the invention, the maturation storage of the active substance matrix (14) can be followed by cooling at a temperature between 3 and 10° C. This has a positive effect on the cohesion and thus on the shear stability of the matrix (14) and is favourable to its mechanical strength in the case of punching or cutting.

Figure 2:
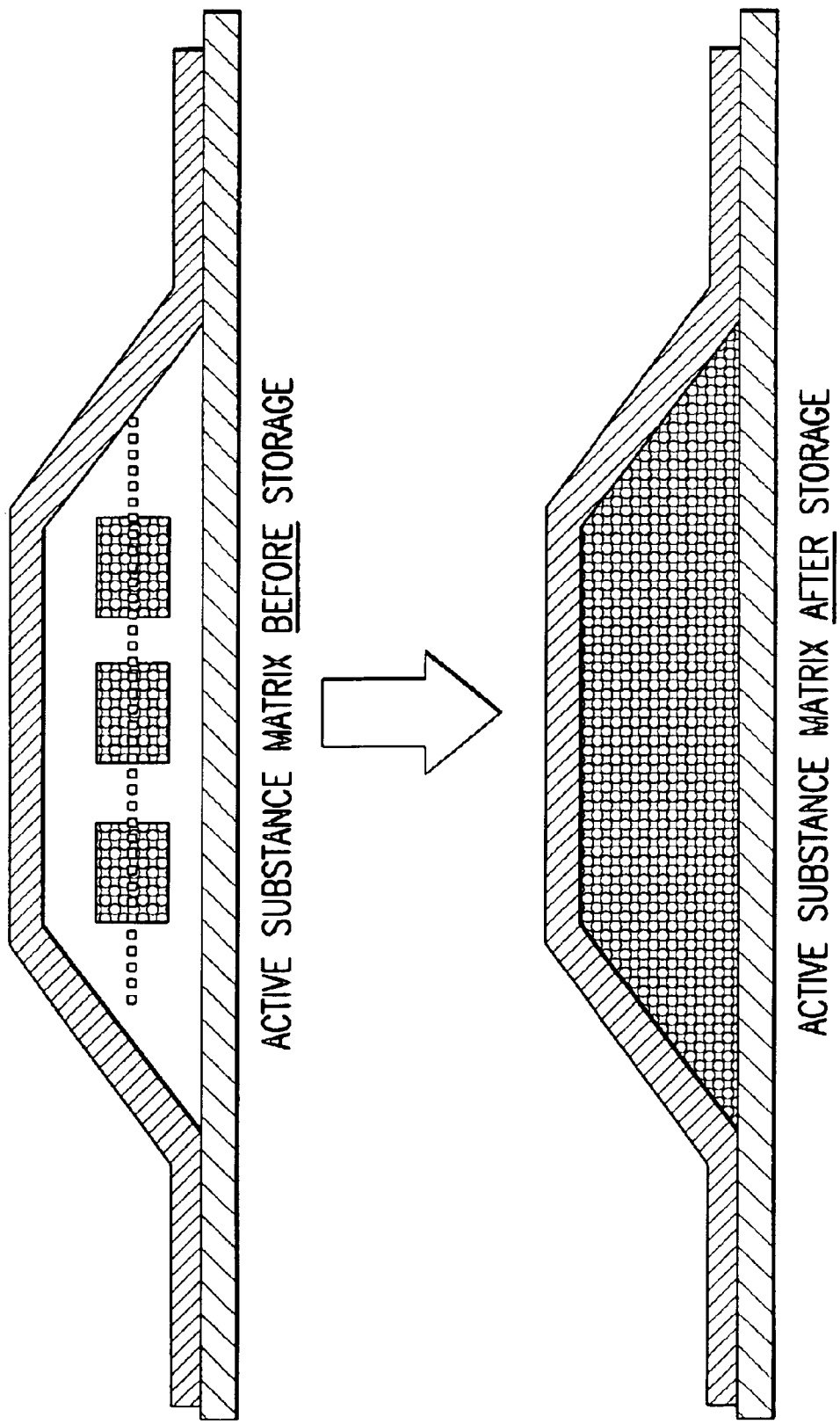
FIG. 2 is a sectional view showing the active substance matrix before and after storage.

In further process steps, the single-layer matrix produced in accordance with the invention, as shown in FIG. 2, is combined with other functional layers and then processed to give individual plaster-like formulations.

The invention is described below with reference to an example, which represents a preferred embodiment of the invention.

EXAMPLE

In FIG. 1, the web (1*a*) is a laminate whose width, for example, is 54 mm and which, as viewed from bottom to top, consists of a 36 µm thick PET support film, a 125 g/m² base material layer made of polyacrylate, and a siliconized protective layer (95 g/m² paper). The second web of laminate (2*a*) is also 54 mm wide and comprises, as viewed from bottom to top, 95 g/m² siliconized paper, a 125 g/m² base material layer, identical with that of the laminate (1*a*), and an 80 µm thick siliconized PE protective film. Before metering, the protective layers (3, 4) of the two laminates (1*a*, 2*a*) are peeled off and taken up by the winders (5) and (6). The remaining laminates are taken into the laminating unit (13) such that the weblike base mat rial layer of the laminate (1*a*) is congruent with the web lying on the counter-roller.

The active substance formulation, which has a viscosity of 1100 mpa.s and comprises 52.46% by weight dimethoate, 34.76% by weight N-methylpyrrolidone and 12.78% by weight colloidal silica, is metered continuously onto the centre of the base material strip (polyacrylate film) of the laminate (1*a*) by means of three applicator nozzles (12), metering taking place at a pump speed of 850 rpm and a machine running speed of 20 m/min. The amounts of active substance applied are 0.386 g per 0.64 m of the laminate (1*a*). Directly after the active substance medium has been metered, it is covered with the second base material layer (2*a*). This operation, referred to as laminating, is carried out under a pressure of 3 bar.

The resultant matrix laminate (14) containing dimethoate is stored at 20° C. for 14 days for the purpose of maturation and subsequently at 6° C. for 24 hours.

The finishing of the formulation, by uniting the matrix (14) with a final cover, and the subsequent processing, take place in a punching and processing unit.

What is claimed is:

1. Process for producing an article in a form of a sheet comprising a single-layer homogeneous matrix containing at least one active substance for an application site, said at least one active substance being selected from crop protection agents, biocides, fertilizers, plant strengtheners, cosmetic active principles and fragrances, said process comprising the following temporally and spatially separate steps:

a) applying the at least one active substance as a flowable medium having a viscosity of at least 1000 mPa·s to at least one of the two layers, identical in composition of a base material, at a pressure ≦12 bar with metering b) placing the two base material layers atop one another so as to enclose the at least one active substance applied, and irreversible joining of the layers with the at least one active substance therebetween under pressure of 2 to 10 bars to form a laminate; and c) storing the laminate for predeterminable duration under defined conditions to effect migration of the at least one active substance into the base material layers and connection of the base material layers at their interfaces to form a single-layer homogeneous matrix in which the at least one active substance is substantially uniformly distributed.

2. Process according to claim 1, wherein the pressure in step b) is 3 to 5 bars.

3. Method for producing a monolithic single layer laminated sheet matrix containing a releasable ingredient, said method comprising performing the steps of:

a) providing first and second matrix base layers, each of said first and second matrix base layers comprising a sheet, having opposite first and second surfaces, of an absorbent and permeable polymeric material capable of absorbing a flowable substance through said first surface, diffusing said flowable substance throughout said polymeric material of said sheet, and uniformly and continuously diffusively releasing said flowable substance through said second surface for a predetermined period of time;

b) providing a flowable substance having a viscosity of at least 1,000 mPa·s; and further performing, in the indicated order, the steps of:

c) storing said flowable substance in an enclosed vessel, in fluid communication with a plurality of distribution outlets, from which said flowable substance is controllably distributable;

d) applying, through said distribution outlets, at a pressure not greater than 12 bars, to said first surface of said sheet of at least one of said first and second matrix base layers at a plurality of locations distributed over said first surface of said sheet, a predetermined amount of said flowable substance, sufficient to diffuse into said polymeric material of said sheets of said first and second matrix base layers, and to release a predetermined amount of said flowable substance through at least one of said second sheet surfaces, continuously for a predetermined period of time;

e) contacting said first surface of said sheet of said first matrix base layer with said first surface of said sheet of said second matrix base layer;

f) applying sufficient pressure to said contacted first and second matrix base layers to irreversibly fuse said first and second matrix base layers to one another with said flowable substance therebetween, forming a monolithic single layer laminate; and g) permitting said flowable material to diffuse through said permeable polymeric material of said sheet of each of said first and second matrix base layers, to effect a distribution of said flowable substance throughout said first and second matrix base layers under a diffusion driving force until a state of dynamic equilibrium is attained.

4. Method according to claim 3, wherein said pressure in step (c) is 2 to 10 bars.

5. Method according to claim 4, wherein said pressure in step (c) is 3 to 5 bars.

6. Method according to claim 3, wherein step (f) is performed for a time of at least 48 hours, and at a temperature not exceeding a degradation temperature of said flowable substance.

7. Method according to claim 6, wherein said temperature is 15–30° C.

8. Method according to claim 7, wherein said temperature is 20–24° C.

9. Method according to claim 3, wherein said flowable substance comprises an active ingredient.

10. Method according to claim 9, wherein said active ingredient is selected from the group consisting of: crop protection agents, biocides, fertilizers, plant strengthening agents, cosmetically active agents, fragrances, and pharmaceutically active agents.

11. Method according to claim 9, wherein said active ingredient comprises one selected from the group consisting of: dimethoate, imidacloprid, fenpropidene, acephate, and acetamiprid.

12. Method according to claim 9, wherein said active ingredient comprises one selected from the group consisting of: Z,E-9,12-tetradecadienol, Z,E-9,12-tetradecadien-1-yl acetate, and mixtures thereof.

13. Method according to claim 9, wherein said active ingredient is selected from the group consisting of: a volatile substance having a measurable vapor pressure at ambient temperature; and a thermally labile substance having a degradation temperature or a temperature at which activity thereof decreases above 50° C.

14. Method according to claim 9, wherein said flowable substance further comprises a tackifier.

15. Method according to claim 9, wherein said active ingredient is self-adhesive.

16. Method according to claim 3, wherein in step (c), said flowable substance is applied to said first surface of said sheet of at least one of said first and second matrix base layers at a plurality of locations distributed over said first surface of said sheet in a predetermined pattern.

17. Method according to claim 16, wherein said pattern comprises one selected from the group consisting of: stripes, dots, and geometric shapes.

18. Method according to claim 3, wherein in step (a), said polymeric material of said first and second matrix base layers comprises at least one compound selected from the group consisting of: ethylene-vinyl acetate copolymers; styrene/butadiene/styrene (SBS) block copolymers; styrene/isoprene/styrene (SIS) block copolymers; polyisobutylenes; polyacrylates; polymethacrylates; polyvinyl esters; polyamide; polyesters; cellulosic compounds; and silicones.

19. Method according to claim 3, wherein said sheet of each said first and second matrix base layers has a weight per unit area of 125 g/m².

20. Method according to claim 3, wherein at least one of said sheet of said first matrix base layer and said sheet of said second matrix base layer has a protective layer on at least one of its said first and second surfaces, such that when there is a protective layer on only one said surface, said protective layer is removable; and when there is a protective layer on each said surface, at least one of said protective layers is removable.

21. Method according to claim 20, wherein said protective layers are peelable.

22. Method according to claim 20, wherein said protective layers are selected from the group consisting of papers, plastics, and textiles.

23. Method according to claim 22, wherein said protective layers are coated with silicone.

24. Method according to claim 20, wherein said protective layer is removed from at least one sheet surface of one of said first and second matrix base layers before step (d).

25. Method according to claim 20, wherein both said sheet of said first matrix base layer and said sheet of said second matrix base layer have a protective layer on at least one of their respective first and second surfaces.

26. Method according to claim 25, wherein both said sheet of said first matrix base layer and said sheet of said second matrix base layer have a protective layer on both of their respective first and second surfaces.

27. Method according to claim 3, wherein said sheet of said first matrix base layer and said sheet of said second matrix base layer are continuous strips.

28. Method according to claim 27, wherein said strips are in rolls.

29. Method according to claim 20, wherein at least one of said first and second surfaces of at least one of said sheet of said first matrix base layer and said sheet of said second matrix base layer has a support layer thereon.

30. Method according to claim 20, wherein said protective layers have a thickness of 80 µm.

31. Method according to claim 29, wherein said support layer has a thickness of 36 µm.

32. Method according to claim 23, wherein said protective layer is a siliconized paper.

33. Method according to claim 32, wherein said siliconized paper has a weight per unit area of 95 g/m².

34. Method according to claim 27, wherein said strips have a width of 54 mm.

35. Method according to claim 9, wherein said flowable substance further comprises an additive.

36. Method according to claim 35, wherein said additive is colloidal silica.

37. Method according to claim 35, wherein said additive is a iscosity increasing agent.

38. Method according to claim 36, wherein said flowable substance comprises 52.46 wt % dimethoate, 34.76 wt. % N-methylpyrrolidone, and 12.78 wt % colloidal silica.

39. Method according to claim 3, wherein there are three distribution outlets.

* * * * *